US012731693B2

(12) United States Patent
Zhang et al.

(10) Patent No.: US 12,731,693 B2
(45) Date of Patent: Sep. 8, 2026

(54) DEEP LEARNING-BASED CANCER PROGNOSIS SURVIVAL PREDICTION METHOD AND DEVICE, AND STORAGE MEDIUM

(71) Applicants: ANKON TECHNOLOGIES CO., LTD, Wuhan (CN); ANX IP HOLDING PTE. LTD., Singapore (SG)

(72) Inventors: Chukang Zhang, Wuhan (CN); Zhiwei Huang, Wuhan (CN); Hao Zhang, Wuhan (CN); Fanhua Ming, Wuhan (CN)

(73) Assignees: ANKON TECHNOLOGIES CO., LTD, Wuhan (CN); ANX IP HOLDING PTE. LTD., Singapore (SG)

( * ) Notice: Subject to any disclaimer, the term of this patent is extended or adjusted under 35 U.S.C. 154(b) by 286 days.

(21) Appl. No.: 18/573,998

(22) PCT Filed: Jun. 22, 2022

(86) PCT No.: PCT/CN2022/100334
§ 371 (c)(1),
(2) Date: Dec. 22, 2023

(87) PCT Pub. No.: WO2022/268102
PCT Pub. Date: Dec. 29, 2022

(65) Prior Publication Data

US 2024/0331868 A1 Oct. 3, 2024

(30) Foreign Application Priority Data

Jun. 22, 2021 (CN) ........................ 202110688757.4

(51) Int. Cl.
*G06T 7/00* (2017.01)
*G06V 10/74* (2022.01)
(Continued)

(52) U.S. Cl.
CPC .......... *G16H 50/30* (2018.01); *G06T 7/0012* (2013.01); *G06V 10/74* (2022.01); *G16H 50/70* (2018.01);
(Continued)

(58) Field of Classification Search
CPC ........ G16H 50/30; G16H 50/70; G16H 50/20; G06T 7/0012; G06T 2207/20081;
(Continued)

(56) References Cited

U.S. PATENT DOCUMENTS

2018/0336395 A1* 11/2018 Madabhushi ........ G06V 10/764
2020/0242756 A1* 7/2020 Madabhushi ............ G06T 7/45
(Continued)

FOREIGN PATENT DOCUMENTS

CN 109635835 A 4/2019
CN 111370128 A 7/2020
(Continued)

OTHER PUBLICATIONS

Cheerla, A. Deep Learning with Multimodal Representation for Pancancer Prognosis Prediction, Bioinformatics, vol. 35, No. 14, Jul. 15, 2019, ISSN: 1367-4803, sections 3-5.

*Primary Examiner* — Ali Bayat
(74) *Attorney, Agent, or Firm* — Treasure IP group, LLC

(57) ABSTRACT

The present invention provides a deep learning-based cancer prognosis survival prediction method and a device, and a storage medium. The method includes: data acquisition: acquiring sample data, where the sample data comprising pathological image data and clinical data of a sample; data preprocessing; prediction model training: training and
(Continued)

evaluating a prediction model to obtain an optimal prediction model; and risk prediction: performing risk prediction on a new sample on the basis of an optimal classifier model and the optimal prediction model. In the method, data features of the pathological image data and clinical data are unified, the prediction model is trained and evaluated to obtain the optimal prediction model, and prognosis risk evaluation is performed on the new sample to enhance the efficiency of diagnosis and treatment in the clinical field and improve the accuracy of risk evaluation results.

7 Claims, 1 Drawing Sheet

(51) Int. Cl.
*G16H 50/30* (2018.01)
*G16H 50/70* (2018.01)

(52) U.S. Cl.
CPC ............... *G06T 2207/20081* (2013.01); *G06T 2207/20084* (2013.01); *G06T 2207/30092* (2013.01); *G06V 2201/032* (2022.01)

(58) Field of Classification Search
CPC G06T 2207/20084; G06T 2207/30092; G06V 10/74; G06V 2201/032; G06F 18/241
USPC .......................................................... 382/128
See application file for complete search history.

(56) References Cited

U.S. PATENT DOCUMENTS

| | | | | |
|---|---|---|---|---|
| 2020/0323893 | A1* | 10/2020 | Shea | C12Q 1/6886 |
| 2021/0035694 | A1* | 2/2021 | Madabhushi | G06N 3/0464 |
| 2021/0133572 | A1* | 5/2021 | Choi | G06N 20/20 |
| 2021/0233659 | A1* | 7/2021 | Chennubhotla | G06F 18/211 |
| 2022/0148733 | A1* | 5/2022 | Arteta | G16H 30/40 |
| 2022/0180514 | A1* | 6/2022 | Vlasimsky | A61B 6/5217 |
| 2024/0037747 | A1* | 2/2024 | Raedt | G06N 3/09 |

FOREIGN PATENT DOCUMENTS

| | | | |
|---|---|---|---|
| CN | 112184658 | A | 1/2021 |
| CN | 112262440 | A | 1/2021 |
| CN | 112687327 | A | 4/2021 |
| EP | 3573072 | A1 | 11/2019 |

* cited by examiner

DEEP LEARNING-BASED CANCER PROGNOSIS SURVIVAL PREDICTION METHOD AND DEVICE, AND STORAGE MEDIUM

CROSS-REFERENCE OF RELATED APPLICATIONS

The application is a National Phase Application of PCT International Application No. PCT/CN2022/100334, International Filing Date Jun. 22, 2022, published Dec. 29, 2022 as International Publication Number WO2022/268102A1, which claims priority from Chinese Patent Application No. 202110688757.4, filed Jun. 22, 2021, all of which are incorporated herein by reference in their entirety.

FIELD OF INVENTION

The present invention relates to the fields of computer technology, image analysis and processing, and clinical diagnostics, specifically to the artificial intelligence algorithms, with machine learning and deep learning as representatives, and the techniques related to clinical statistics, and more particularly to a deep learning-based cancer prognosis survival prediction method, a device, and a storage medium.

BACKGROUND

Survival analysis refers to a series of statistical methods employed to investigate the occurrence of an event of interest. Unlike traditional regression problems, the objective of survival analysis is to calculate the probability of occurrence of a specific event at a given time and then estimate the survival status of subjects over time, rather than merely predicting a target variable. Common survival analysis techniques include the KM (Kaplan-Meier) method and Cox regression (Cox proportional hazards model), etc. The KM method is a non-parametric method that estimates the survival probability based on the observed survival time, belonging to the category of univariable analysis. On the other hand, Cox regression is a semi-parametric regression model that considers survival outcome and survival time as dependent variables, while analyzing the impact of various factors on the survival period. Survival analysis finds extensive applications in clinical and biostatistical fields, with the prognosis prediction of cancer being a typical application scenario.

Currently, the prognosis prediction of cancer primarily involves diagnostic analysis of medical image data (such as pathological slice images). However, in reality, clinical data also serves as a crucial basis for clinical diagnosis. The existing method of diagnosing and predicting based on one-sided data, particularly the medical image data, does not achieve high accuracy.

Therefore, how to effectively combine medical image data with clinical data and perform diagnostic analysis and prediction thereof, is a problem that needs to be solved urgently.

SUMMARY OF THE INVENTION

An object of the present invention is to provide a deep learning-based cancer prognosis survival prediction method and device, and a storage medium.

To achieve one of above objects of the present invention, an embodiment of the present invention provides a deep learning-based cancer prognosis survival prediction method, comprising:

data acquisition: acquiring sample data, where the sample data comprises pathological image data and clinical data of a sample;

data preprocessing: training and evaluating a deep learning classifier model on the basis of the sample data to obtain an optimal classifier model; using the optimal classifier model to preprocess the sample data, extracting data features of cancerous regions in the pathological image data and obtaining a first preprocessed data for each sample, converting the clinical data for computer language recognition and obtaining a second preprocessed data for each sample;

prediction model training: training and evaluating a prediction model by using all the first preprocessed data and all the second preprocessed data to obtain an optimal prediction model;

risk prediction: performing risk prediction on a new sample on the basis of the optimal classifier model and the optimal prediction model.

In an embodiment of the present invention, the process of training the prediction model using the first preprocessed data and the second preprocessed data of a sample comprises:

compressing the first preprocessed data to obtain a third preprocessed data with the same data type as the second preprocessed data, splicing the second preprocessed data and the third preprocessed data into a feature vector, and compressing the feature vector and activating through an activation function to obtain a final prediction result.

In an embodiment of the present invention, the step of "training and evaluating a deep learning classifier model on the basis of the sample data to obtain an optimal classifier model" comprises:

training and evaluating the classifier model by a weakly supervised deep learning and with the pathological image data of the sample as input data, to obtain the optimal classifier model, where the pathological image data comprises cancerous pathological sections and non-cancerous pathological sections collected in a predefined ratio.

In an embodiment of the present invention, the step of "training and evaluating the classifier model by a weakly supervised deep learning and with the pathological image data of the sample as input data" comprises:

performing horizontal and vertical traversal of each pathological image data by using a fixed-size sliding window at a specified step size, to generate a plurality of sliding window regions with the same labels as the corresponding pathological image data; and training and evaluating a classifier model based on a cross entropy loss function using all the sliding window regions, to obtain the optimal classifier model.

In an embodiment of the present invention, the step of "extracting data features of cancerous regions in the pathological image data and obtaining a first preprocessed data for each sample" comprises:

inputting cancerous pathological sections into the optimal classifier model, and selecting the first k image regions with the highest cancer probability from each cancerous pathological section to obtain the first preprocessed data.

In an embodiment of the present invention, the prediction model comprises two layers, and the process of training and evaluating the prediction model using the first preprocessed data and the second preprocessed data comprises:

in a first layer of the prediction model, using the optimal classifier model with a fully connected layer removed as a feature extractor, extracting a feature vector from each image region of the first preprocessed data, where the feature vector extracted from each image region is a first feature vector; compressing the first feature vector using a multilayer perception deep learning algorithm with two hidden layers, obtaining a single feature value with a length of 1 for each first feature vector, and horizontally splicing the single feature value and the second preprocessed data to obtain a second feature vector;

in a second layer of the prediction model, using an optimization training based on a negative log-likelihood loss function and a concordance index as the performance metric for the prediction model, outputting probability values by an activation function after compressing each second feature vector, where the average of all probability values is a prognosis risk indicator for each sample.

In an embodiment of the present invention, the pathological image data for each sample is prepared using a uniform staining method and a uniform magnification factor;

the clinical data for each sample are indicators of cancer treatment and assessment, comprise gender, age, lesion size, pathological stage, T/N/M stage, and histological stage.

In an embodiment of the present invention, the clinical data comprises discrete variables and continuous variables, and the step of "converting the clinical data for computer language recognition" comprises:

filling the discrete variables with missing values through independent entries;

filling the continuous variables with missing values through overall mean;

encoding the discrete variables by digitizing.

To achieve one of above objects of the present invention, an embodiment of the present invention provides an electronic device, comprising a memory and a processor, where, the memory stores a computer program that can run on the processor, and the processor executes the computer program to implement steps of the deep learning-based cancer prognosis survival prediction method.

To achieve one of above objects of the present invention, an embodiment of the present invention provides a computer-readable storage medium for storing a computer program. The computer program is executed by the processor to implement the steps of the deep learning-based cancer prognosis survival prediction method.

In the deep learning-based cancer prognosis survival prediction method according to the embodiments of the present invention, the data features of pathological image data and clinical data are unified, the prediction model is trained and evaluated based on the pathological image data and clinical data with unified data features to obtain the optimal prediction model, and prognosis risk evaluation is performed on the new sample to enhance the efficiency of diagnosis and treatment in the clinical field and improve the accuracy of risk evaluation results.

DETAILED DESCRIPTION

The present invention can be described in detail below with reference to the accompanying drawings and preferred embodiments. However, the embodiments are not intended to limit the invention, and the structural, method, or functional changes made by those skilled in the art in accordance with the embodiments are included in the scope of the present invention.

Figure 1:
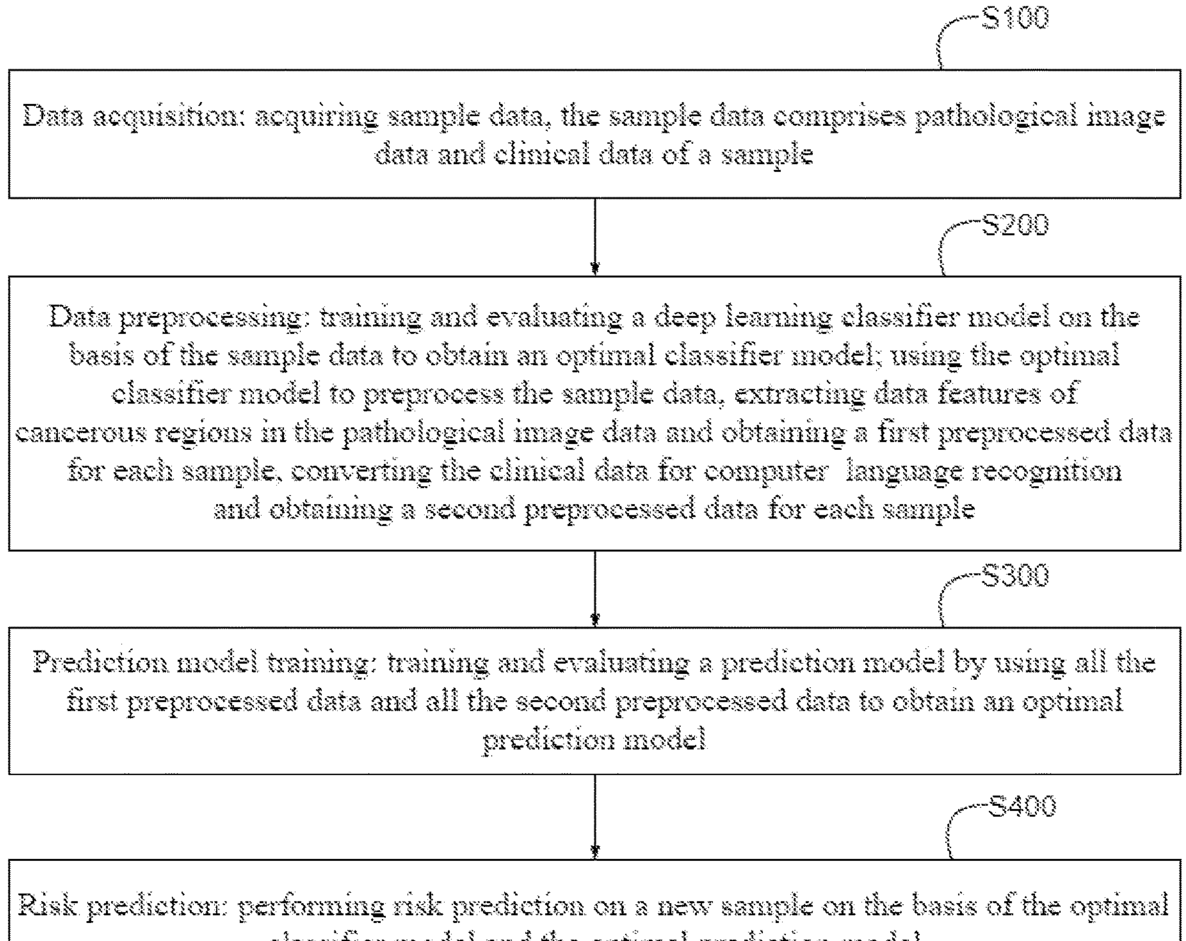
FIG. 1 is a process flow diagram of a deep learning-based cancer prognosis survival prediction method according to one embodiment of the present invention.
Figure 2:
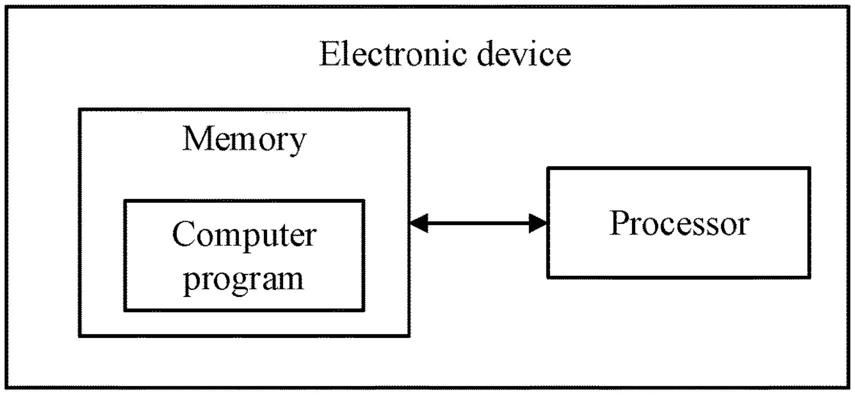
FIG. 2 is a schematic illustration of an electronic device of the present invention.

Referring to FIG. 1, the present invention provides a deep learning-based cancer prognosis survival prediction method. The method comprising the following steps.

Step S100, data acquisition: acquiring sample data, where the sample data comprises pathological image data and clinical data of a sample.

The step S100 is primarily utilized for collecting prognosis information of cancer patients, where the relevant prognosis information of each cancer patient is a piece of cancer sample data. The sample data comprises pathological image data and clinical data of a sample.

However, in order to train the subsequent model, the step S100 also collects relevant information from non-cancer patients corresponding to cancer patients. The relevant information of each non-cancer patient is a piece of non-cancer sample data. The cancer sample data and non-cancer sample data together constitute all sample data, i.e. constituting a sample dataset, based on a predefined ratio. Preferably, the predefined ratio is 1:1.

Further, the pathological image data for each sample is prepared using a uniform staining method and a uniform magnification factor. Specifically, the pathological sections corresponding to the pathological image data are prepared using a uniform Hematoxylin-Eosin staining (HE staining) method and have the same imaging magnification factor (e.g., 5× or 10×).

The clinical data for each sample are indicators of cancer treatment and assessment, comprise, but not limited to, gender, age, lesion size, pathological stage, T/N/M (Tumor Node Metastasis Classification) stage, and histological stage. For data collection pertaining to a specific feature, adhering to unified standards and units is necessary.

Each sample is labeled, and the label information comprises survival status and survival time as of the observation cutoff time. The survival status comprises survival (0) and death (1), and the unit for survival time is years.

Step S200, data preprocessing: training and evaluating a deep learning classifier model on the basis of the sample data to obtain an optimal classifier model (the optimal classifier model is an optimal deep learning classifier model); using the optimal classifier model to preprocess the sample data, extracting data features of cancerous regions in the pathological image data and obtaining a first preprocessed data for each sample, converting the clinical data for computer language recognition, and obtaining a second preprocessed data for each sample.

The data preprocessing primarily comprises separate preprocessing for pathological image data and clinical data within the sample data. For the preprocessing of pathological image data, it is necessary to initially train and evaluate the classifier model based on the pathological image data to obtain the optimal classifier model. Subsequently, the optimal classifier model is utilized to extract data features from the cancerous regions of the pathological image data in cancer samples.

Preferably, the step of "training and evaluating a deep learning classifier model on the basis of the sample data to obtain an optimal classifier model" comprises:

- training and evaluating the classifier model by a weakly supervised deep learning and with the pathological image data of the sample as input data, to obtain the optimal classifier model, where the pathological image data comprises cancerous pathological sections and non-cancerous pathological sections collected in the predefined ratio.

Further, the step of "training and evaluating the classifier model by a weakly supervised deep learning and with the pathological image data of the sample as input data" comprises:

- performing horizontal and vertical traversal of each pathological image data by using a fixed-size sliding window at a specified step size, to generate a plurality of sliding window regions with the same labels as the corresponding pathological image data; and
- training and evaluating a classifier model based on a cross entropy loss function using all the sliding window regions, to obtain the optimal classifier model.

In an embodiment, the step S200 comprises the following steps.

Step S210, performing horizontal and vertical reversal of the pathological image data of each sample using a fixed-size square sliding window (e.g., 224*224 pixels) at a predetermined step size (e.g., 10% or 15% of the side length of the sliding window), to obtain a plurality of small sliding window regions corresponding to each pathological image data, the labels of the sliding window regions being consistent with the labels of the corresponding complete pathological image data. The labels can be benign or malignant.

Step S220, dividing the pathological image data of all samples into training set and validation set on a per-complete-sample basis, and establishing a deep learning classifier based on convolutional neural network (CNN) for binary classification prediction training.

The classifier can be selected from various existing deep learning models, such as the ResNet (Residual Network) model or VGG (Visual Geometry Group Network) model based on CNN. The cross entropy loss function is used for model optimization by the formula:

$$L = -\sum_{i=1}^{N} y^{(i)} \log \hat{y}^{(i)} + (1 - y^{(i)}) \log(1 - \hat{y}^{(i)}),$$

where N is the number of samples, $y^{(i)}$ is the true label (0 or 1) of the i-th sample, and $\hat{y}^{(i)}$ is the positive probability value output by the i-th sample through a Sigmoid or Softmax activation function. The evaluation metric for the model is the classification accuracy of the samples. The final prediction probability result for each sample is the output mean of the s sliding window regions with the highest positive probability, and the value of s can be 32, 64, or 128, preferably 128.

Step S230, after the model training converges stably to achieve optimal results (i.e., obtaining the optimal classifier model), outputting the prediction probability results of the sliding window regions corresponding to the pathological image data of each cancer sample, and saving the top-left coordinates (xi, yi) of the k sliding windows regions with the highest probability values, to obtain the first preprocessed data for each sample. Here, the value of k may be 32, 64, or 128, with 128 being the preferred option.

Step S240, preprocessing the clinical data to obtain the second preprocessed data for each sample.

The clinical data comprises discrete variables and continuous variables, generally collected in tabular form. The tabular information is then transformed into a format recognizable by computer language, comprising:

- filling the discrete variables with missing values (e.g., pathological staging) through independent entries, for example, filling in the discrete variables with missing values with "N/A";
- filling the continuous variables with missing values through overall mean; here, continuous variables may be, for example, age or lesion diameter;
- encoding the discrete variables by digitizing; for example, encoding gender: 0 for male, 1 for female; encoding histological staging: 0 for G1 stage, 1 for G2 stage, 2 for G3 stage, 3 for N/A.

Step S300, prediction model training: training and evaluating a prediction model by using all the first preprocessed data and all the second preprocessed data to obtain an optimal prediction model.

This step mainly comprises unifying the data features of pathological image data and clinical data, and training and evaluating the prediction model based on the pathological image data and clinical data with unified data features to obtain the optimal prediction model.

In a preferred embodiment, the process of training the prediction model using the first preprocessed data and the second preprocessed data of a sample comprises the following steps:

- compressing the first preprocessed data to obtain a third preprocessed data with the same data type as the second preprocessed data, splicing the second preprocessed data and the third preprocessed data into a feature vector, and compressing the feature vector and activating through an activation function to obtain a final prediction result.

On the basis of the embodiment of step S200, in another preferred embodiment, the prediction model comprises two layers, and the process of "training and evaluating the prediction model using the first preprocessed data and the second preprocessed data" comprises the following steps.

Step S310: in the first layer of the prediction model, using the optimal classifier model with the fully connected layer removed as a feature extractor, extracting a feature vector from each image region of the first preprocessed data, the feature vector extracted from each image region being a first feature vector; compressing the first feature vector using a MLP (Multilayer Perception) deep learning algorithm with two hidden layers, obtaining a single feature value with a length of 1 for each first feature vector, and horizontally splicing the single feature value and the second preprocessed data to obtain a second feature vector.

Specifically, based on the k sliding window images corresponding to the pathological image data for each cancer sample obtained in step S230, the trained optimal classifier model (e.g. the RegNet model) is used, with the fully connected layer removed, as a feature extractor to extract the feature vectors of s sliding window images for each sample (one sliding window image corresponds to one feature vector). Based on the network architecture design of RegNet, the length of the feature vectors is 608. Next, a MLP deep learning algorithm with two hidden layers is designed to compress the feature vectors of these sliding window regions. The SELU (Scaled Exponential Linear Unit) activation function is used, and its formula is:

$$selu = \lambda \begin{cases} x & \text{if } x > 0 \\ \alpha ex - \alpha & \text{if } x \leq 0 \end{cases},$$

where $\lambda \in [1, 1.5]$, $\alpha \in [1.5, 2]$. The input feature vector, after passing through the first hidden layer, is compressed from a length of 608 to 64. Subsequently, it undergoes further compression to 32 after passing through the second hidden layer. Finally, the output is a single feature value of length 1. The result output from the MLP is horizontally spliced with the M pieces of clinical data processed in step S240, to obtain a new feature vector of length M+1. In other words, each sample can have k (k=128) new feature vectors, and within each new feature vector, the values related to clinical data can be identical.

Step S320, in the second layer of the prediction model, using the optimization training based on a negative log-likelihood loss function and a concordance index as the performance metric for the prediction model, outputting probability values by an activation function after compressing each second feature vector. The average of all probability values is the prognosis risk indicator for each sample.

For the newly generated feature vectors from the previous step, an MLP with SELU activation function is used as the prognosis risk prediction algorithm. The model takes a vector of length M+1 as input, compresses it through one hidden layer, and outputs a single feature value of length 1. Finally, an additional Sigmoid activation function layer is applied to produce a probability value. The average of the probability values from all k (k=128) records for each sample is the prognosis risk indicator for that sample. For model training, the negative log-likelihood loss function is selected, and the concordance index (C-Index) of the dataset is used as the performance metric for the model.

Step S400, risk prediction: performing risk prediction on a new sample on the basis of the optimal classifier model and the optimal prediction model.

Specifically, the step S400 comprises the following steps.

Step S410, collecting data from the cancer patients to be predicted as new samples, comprising:

- pathological image data (pathological sections), obtained using the same staining method (e.g., HE staining) and magnification factor (e.g., 10×) as used in the model training;
- clinical data (M items), requiring the same data collection standards and units as the corresponding clinical features used in model training.

Step S420, preprocessing the data of the new samples to obtain:

- coordinates of the 128 blocks of size 224*224 with the highest malignant probability on the pathological sections;
- clinical data with missing value filling up and digital encoding completed.

Step S430, loading structure and parameters of the optimal prediction model, and using the preprocessed data of the new samples as input, to obtain the corresponding prognosis risk score. The score can be used as additional diagnostic information for the prognosis of cancer patients, provided for reference to medical professionals (where a low score indicates a good prognosis, and a high score indicates a poor prognosis).

In an embodiment of the deep learning-based cancer prognosis survival prediction method, the cancer refers to gastric cancer, and the method comprises the following steps.

Step 1, collecting gastric cancer sample dataset. The data of each gastric cancer sample comprises pathological sections (pathological image data) and clinical data. Pathological sections comprise clearly identifiable tumor lesion areas and are prepared using a uniform staining method (HE staining method is chosen in the embodiment). Additionally, it's crucial to note that to ensure model accuracy, all pathological sections must have a consistent imaging magnification factor (10× is selected in the embodiment). Clinical data consist of a plurality of indicators for gastric cancer treatment determination, comprising discrete variables (such as gender, pathological stage, T/N/M stage, and histological stage, totaling 6) and continuous variables (such as age and lesion size, totaling 2). Each sample should have complete label information, i.e., survival status (0 for survival, 1 for death) and survival time (unit needs to be consistent, here it's in years).

Step 2, data preprocessing. Both pathological sections and clinical data need to undergo preprocessing. The specific procedures are as follows.

Step 2.1, pathological sections: extracting of coordinates of regions with the highest malignant probability from the pathological sections. The available method is combining the pathological sections of normal patients and using the weakly supervised deep learning to train a classifier model to output regions with high positive probabilities. Specific implementation procedures are:

- step 2.11, collecting pathological sections from normal samples, ensuring the number of normal samples is roughly equivalent to the gastric cancer samples collected in step 1; where the pathological sections of the gastric cancer samples and normal samples constitute the entire sample dataset; where the sample dataset is used as training data for the gastric cancer/non-gastric cancer classifier model and is randomly split into a training set and a validation set at a ratio of 70%:30%;
- step 2.12: performing horizontal and vertical reversal of the original pathological sections for each sample using a fixed-size square sliding window (e.g., 224*224 pixels) at a specific step size (e.g., 10% of the side length of the sliding window, approximately 22 pixels), to generate a plurality of small sliding window regions, the labels of the sliding window regions being consistent with the corresponding pathological sections (normal 0 or gastric cancer 1);
- step 2.13: using a convolutional neural network (CNN) model (here, RegNet developed by Facebook is selected) with the cross entropy loss function to train the classifier model for all generated sliding window regions, where the evaluation metric is the classification accuracy of the sample; where the output mean of the s sliding window regions with the highest probability for each sample is considered its prediction probability result (s may be 32, 64, or 128, preferably s=128); where the algorithm is trained until stable convergence to achieve optimal results (accuracy, sensitivity, and specificity all exceeding 90%), and the structure weight of the model is saved for subsequent use (i.e., obtain the optimal classifier model);
- step 2.14, loading the saved structure weight of the model from the previous step, outputting and sorting the prediction probability results of all sliding window regions for the pathological sections of each gastric cancer sample, selecting the coordinates of the k regions with the highest probability, and retaining their coordinate information (k is chosen as 128).

Step 2.2, clinical data: mainly filling missing values and digital encoding of discrete variables for computer language recognition of clinical data. The specific method is as follows:

step 2.21, missing values filling: for discrete variables (e.g., pathological staging), missing records are filled with independent entries (e.g., "N/A"); for continuous variables (e.g., age or lesion diameter), missing records are filled with the overall mean or median, and here, the mean is selected;

step 2.22, digital encoding: discrete variables are encoded by digitizing for computer language recognition, such as encoding for gender (male: 0, female: 1) or histological staging (G1 stage: 0, G2 stage: 1, G3 stage: 2, N/A: 3).

Step 2.3, after completing the preprocessing of gastric cancer sample data, randomly splitting the sample dataset into a training set and a validation set at a ratio of 70%:30%, where the training set is used to train the model, and the validation set is used to verify the efficiency of the model.

Step 3, Model training: designing a machine learning algorithm with two layers, where the input of the mode comprises both pathological sections and clinical data. The method is as follows.

Step 3.1, first layer of model: based on the coordinates of the k sliding window regions with the highest positive probability in the pathological sections of each gastric cancer sample in step 2.14, obtaining k region images of size 224*224 highly suspicious regions, and using the trained optimal classifier model (RegNet model) saved in the step 2.13 with the fully connected layer removed, as the feature extractor to extract the feature vectors from each region image. Based on the network architecture design of RegNet, the length of the feature vectors is 608. Next, a MLP deep learning algorithm with two hidden layers is designed to compress the feature vectors of these sliding window regions. The SELU activation function is used, and its formula is:

$$selu = \lambda\begin{cases} x & \text{if } x > 0 \\ \alpha ex - \alpha & \text{if } x \leq 0 \end{cases},$$

where $\lambda \in [1, 1.5]$, $\alpha \in [1.5, 2]$.

The input feature vector, after passing through the first hidden layer, is compressed from a length of 608 to 64. Subsequently, it undergoes further compression to 32 after passing through the second hidden layer. Finally, the output is a single feature value of length 1. The result output from the MLP is horizontally spliced with the 8 pieces of clinical data processed in step 2.2, to obtain a new feature vector of length 9. That is, k new feature vectors of length 9 is obtained for each sample.

Step 3.2, Second layer of model: for the newly generated feature vectors from the previous step, an MLP with SELU activation function is used as the prognosis risk prediction algorithm. The model takes a vector of length 9 as input, compresses it through one hidden layer, and outputs a single feature value of length 1. Finally, an additional Sigmoid activation function layer is applied to output a probability value. The output mean of all k (k=128) records is the prognosis risk indicator for the corresponding sample. For model training, the negative log-likelihood loss function is selected, and the C-Index of the dataset is used as the performance metric for the model.

In the embodiment, the data is trained to convergence with the C-Index of the training set exceeding 0.7 and the C-Index of the validation set stabilizing around 0.65 to obtain the optimal prediction model. The structure and parameters of the optimal prediction model are saved for testing of new sample data.

Step 4, data prediction: The saved structure and parameters of the optimal prediction model from the previous step can be used to predict new, unlabeled samples (pathological sections and clinical data), and the output risk score is then used to evaluate the prognosis quality of the patient. The score can be used as auxiliary information for medical professionals, aiding them in evaluating the prognosis of gastric cancer patients.

In the deep learning-based cancer prognosis survival prediction method according to the embodiments of the present invention, the data features of pathological image data and clinical data are unified, the prediction model is trained and evaluated based on the pathological image data and clinical data with unified data features to obtain the optimal prediction model, and prognosis risk evaluation is performed on the new sample to enhance the efficiency of diagnosis and treatment in the clinical field and improve the accuracy of risk evaluation results.

The present invention further provides an electronic device, comprising a memory and a processor. The memory stores a computer program that can run on the processor, and the processor executes the computer program to implement any of the steps in the above-mentioned deep learning-based cancer prognosis survival prediction method. In other words, the electronic device can implement any of the steps in various embodiments of the deep learning-based cancer prognosis survival prediction method.

The present invention further provides a computer-readable storage medium for storing a computer program. The computer program is executed by the processor to implement any of the steps in the above-mentioned deep learning-based cancer prognosis survival prediction method. In other words, the computer-readable storage medium can implement any of the steps in various embodiments of the deep learning-based cancer prognosis survival prediction method.

It should be understood that, although the description is described in terms of embodiments, not every embodiment merely comprises an independent technical solution. The description is recited in such a manner only for the sake of clarity, those skilled in the art should have the description as a whole, and the technical solutions in each embodiment may also be combined as appropriate to form other embodiments that can be understood by those skilled in the art.

The series of detailed descriptions set forth above are only specific descriptions of feasible embodiments of the present invention and are not intended to limit the scope of protection of the present invention. On the contrary, many modifications and variations are possible within the scope of the appended claims.

The invention claimed is:

1. A deep learning-based cancer prognosis survival prediction method, comprising:

acquiring sample data, wherein the sample data comprises pathological image data and clinical data of a sample; training and evaluating a deep learning classifier model on the basis of the sample data to obtain an optimal classifier model; using the optimal classifier model to preprocess the sample data, extracting data features of cancerous regions in the pathological image data and obtaining a first preprocessed data for each sample, converting the clinical data for computer language recognition and obtaining a second preprocessed data for each sample; training and evaluating a prediction model by using all the first preprocessed data and all the second preprocessed data to obtain an optimal prediction model; performing risk prediction on a new sample on the basis of the optimal classifier model and the optimal prediction model; wherein the step of "training and evaluating a deep learning classifier model on the basis of the sample data to obtain an optimal classifier model" comprises:

training and evaluating the classifier model by a weakly supervised deep learning and with the pathological image data of the sample as input data, to obtain the optimal classifier model, wherein the pathological image data comprises cancerous pathological sections and non-cancerous pathological sections collected in a predefined ratio; wherein the step of "extracting data features of cancerous regions in the pathological image data and obtaining a first preprocessed data for each sample" comprises:

inputting cancerous pathological sections into the optimal classifier model, and selecting the first k image regions with the highest cancer probability from each cancerous pathological section to obtain the first preprocessed data; wherein the prediction model comprises two layers, and the process of training and evaluating the prediction model using the first preprocessed data and the second preprocessed data comprises: in a first layer of the prediction model, using the optimal classifier model with a fully connected layer removed as a feature extractor, extracting a feature vector from each image region of the first preprocessed data, wherein the feature vector extracted from each image region is a first feature vector; compressing the first feature vector using a multilayer perception deep learning algorithm with two hidden layers, obtaining a single feature value with a length of 1 for each first feature vector, and horizontally splicing the single feature value and the second preprocessed data to obtain a second feature vector; in a second layer of the prediction model, using an optimization training based on a negative log-likelihood loss function and a concordance index as the performance metric for the prediction model, outputting probability values by an activation function after compressing each second feature vector, wherein the average of all probability values is a prognosis risk indicator for each sample.

2. The deep learning-based cancer prognosis survival prediction method of claim 1, wherein the process of training the prediction model using the first preprocessed data and the second preprocessed data of a sample comprises:

compressing the first preprocessed data to obtain a third preprocessed data with the same data type as the second preprocessed data, splicing the second preprocessed data and the third preprocessed data into a feature vector, and compressing the feature vector and activating through an activation function to obtain a final prediction result.

3. The deep learning-based cancer prognosis survival prediction method of claim 1, wherein the step of "training and evaluating the classifier model by a weakly supervised deep learning and with the pathological image data of the sample as input data" comprises:

performing horizontal and vertical traversal of each pathological image data by using a fixed-size sliding window at a specified step size, to generate a plurality of sliding window regions with the same labels as the corresponding pathological image data; and training and evaluating a classifier model based on a cross entropy loss function using all the sliding window regions, to obtain the optimal classifier model.

4. The deep learning-based cancer prognosis survival prediction method of claim 1, wherein the pathological image data for each sample is prepared using a uniform staining method and a uniform magnification factor;

the clinical data for each sample are indicators of cancer treatment and assessment, comprise gender, age, lesion size, pathological stage, T/N/M stage, and histological stage.

5. The deep learning-based cancer prognosis survival prediction method of claim 1, wherein the clinical data comprises discrete variables and continuous variables, and the step of "converting the clinical data for computer language recognition" comprises:

filling the discrete variables with missing values through independent entries;

filling the continuous variables with missing values through overall mean;

encoding the discrete variables by digitizing.

6. An electronic device, comprising a memory and a processor, wherein the memory stores a computer program that runs on the processor, and the processor executes the program to implement steps of a deep learning-based cancer prognosis survival prediction method, wherein the method comprises: acquiring sample data, wherein the sample data comprises pathological image data and clinical data of a sample; training and evaluating a deep learning classifier model on the basis of the sample data to obtain an optimal classifier model; using the optimal classifier model to preprocess the sample data, extracting data features of cancerous regions in the pathological image data and obtaining a first preprocessed data for each sample, converting the clinical data for computer language recognition and obtaining a second preprocessed data for each sample; training and evaluating a prediction model by using all the first preprocessed data and all the second preprocessed data to obtain an optimal prediction model; performing risk prediction on a new sample on the basis of the optimal classifier model and the optimal prediction model.

7. A non-transitory computer-readable storage medium having stored thereon a computer program, wherein the computer program is executed by a processor to implement steps of a deep learning-based cancer prognosis survival prediction method, wherein the method comprises:

acquiring sample data, wherein the sample data comprises pathological image data and clinical data of a sample; training and evaluating a deep learning classifier model on the basis of the sample data to obtain an optimal classifier model; using the optimal classifier model to preprocess the sample data, extracting data features of cancerous regions in the pathological image data and obtaining a first preprocessed data for each sample, converting the clinical data for computer language recognition and obtaining a second preprocessed data for each sample; training and evaluating a prediction model by using all the first preprocessed data and all the second preprocessed data to obtain an optimal prediction model; performing risk prediction on a new sample on the basis of the optimal classifier model and the optimal prediction model.

* * * * *